(12) United States Patent
Baevsky et al.

(10) Patent No.: US 11,279,727 B2
(45) Date of Patent: Mar. 22, 2022

(54) ANTI-VIRAL COMPOUNDS AND METHODS OF USE

(71) Applicant: Metro International Biotech, LLC, Worcester, MA (US)

(72) Inventors: Matthew Baevsky, Worcester, MA (US); Bruce Szczepankiewicz, Worcester, MA (US); Karen Lavery, Worcester, MA (US); David J. Livingston, Worcester, MA (US)

(73) Assignee: Metro International Biotech, LLC, Worcester, MA (US)

( * ) Notice: Subject to any disclaimer, the term of this patent is extended or adjusted under 35 U.S.C. 154(b) by 0 days.

(21) Appl. No.: 17/399,445

(22) Filed: Aug. 11, 2021

(65) Prior Publication Data

US 2021/0388019 A1 Dec. 16, 2021

Related U.S. Application Data (63) Continuation of application No. PCT/US2021/037438, filed on Jun. 15, 2021.

(60) Provisional application No. 63/084,858, filed on Sep. 29, 2020, provisional application No. 63/039,162, filed on Jun. 15, 2020.

(51) Int. Cl.
*C07H 19/048* (2006.01)
*A61P 31/14* (2006.01)
*A61K 9/00* (2006.01)

(52) U.S. Cl.
CPC ......... *C07H 19/048* (2013.01); *A61K 9/0053* (2013.01); *A61P 31/14* (2018.01)

(58) Field of Classification Search
CPC ...... C07H 19/048; A61P 31/14; A61K 9/0053
See application file for complete search history.

(56) References Cited

U.S. PATENT DOCUMENTS

| 9,487,544 B2 | 11/2016 | Cho et al. |
| 2013/0018013 A1 | 1/2013 | Francom et al. |
| 2019/0275063 A1 | 9/2019 | Chun et al. |

OTHER PUBLICATIONS

Amirian et al. (One Health, vol. 9 (2020) 100128).*
Invitation to Pay Additional Fees for International Application No. PCT/US21/37438 dated Aug. 27, 2021.
Makarov et a., "Syntheses and chemical properties of B-nicotinamide riboside and its analogues and derivatives," Beilstein J Org Chem, 15: 401-430 (2019).
Mehellou et al., "The ProTide Prodrug Technology: From the Concept to the Clinic," Journal of Medicinal Chemistry, 61: 2211-2226 (2018).
International Search Report and Written Opinion for International Application No. PCT/US2021/037438 dated Nov. 10, 2021.

* cited by examiner

*Primary Examiner* — Shaojia A Jiang
*Assistant Examiner* — Michael C Henry
(74) *Attorney, Agent, or Firm* — David P. Halstead; Foley Hoag LLP (57) ABSTRACT

The present disclosure relates to compounds and compositions for use in treating disease, such as viral infection. As disclosed herein, the compounds include an "NMN-like" moiety linked to another moiety with biological activity upon administration. In some cases, the disease to be treated is infection with viruses. Such viruses include coronaviruses, such as SARS, MERS, or COVID-19, HIV, and viruses associated with hepatitis. Further, the invention relates to methods of using such compounds or compositions to promote the increase of intracellular levels of nicotinamide adenine dinucleotide (NAD) in cells and tissues for treating diseases and/or improving cell and tissue survival.

8 Claims, 2 Drawing Sheets

ANTI-VIRAL COMPOUNDS AND METHODS OF USE

CROSS-REFERENCE TO RELATED APPLICATIONS

This application is a continuation of PCT Patent Application Number PCT/US2021/037438, filed Jun. 15, 2021, which claims priority to U.S. Provisional Application No. 63/039,162, filed Jun. 15, 2020, and U.S. Provisional Application No. 63/084,858, filed Sep. 29, 2020, each of which is incorporated herein by reference in its entirety for all purposes.

BACKGROUND

Nicotinamide Adenine Dinucleotide (NAD) is an essential metabolic cofactor. Recent research has indicated that NAD levels decline with age and in certain mammalian disease states, and that therapeutically increasing NAD levels has health benefits. However, NAD is an intracellular metabolite, and does not readily lend itself to external supplementation. It has been suggested that utilizing precursors to the natural synthesis of NAD may be an effective way to increase NAD.

Two exemplary precursors that could be administered to increase NAD are nicotinamide mononucleotide (NMN), which is directly synthesized into NAD, and nicotinamide riboside (NR), which is recycled from the utilization of NAD, into NMN. There are no known dietary or environmental sources of NMN or NR. Accordingly, in order to use these precursors as drugs or supplements, they must be manufactured.

Nicotinamide adenine dinucleotide (NAD) boosting compounds, such as β-Nicotinamide mononucleotide (NMN), have recently gamed attention for use in the treatment, amelioration, mitigation, slowing, arrest, prevention and/or reversal of a wide variety of diseases and conditions, including but not limited to age-associated degenerative changes, such as age-related obesity, age-related increases in blood lipid levels, age-related decreases in insulin sensitivity, age-related decreases in memory function, and age-related changes in eye function such as macular degeneration.

Despite the advances in understanding the biology of NAD, there remains a need for improved compositions and methods of using such compositions for pharmacologic intervention and/or manipulation of the NAD pathway in living cells and tissues, particularly for viral infections such as coronavirus, SARS, MERS, or COVID-19 (also known as SARS-CoV-2).

SUMMARY

The present disclosure relates to compounds and compositions comprising an NAD moiety linked to an antiviral moiety, and compositions and methods of use thereof.

In certain embodiments, the compound has a structure represented by Formula (I):

or a pharmaceutically acceptable salt thereof, wherein
X is $NH_2$ or OH;
$L^1$ wherein each $R^1$ is independently $O^+$, O-alkyl, NH-alkyl, or alkyl; Z is O or NH; n is 0 or 1; * is the point of attachment to the oxygen atom; and ** is the point of attachment to D; and
D is an antiviral moiety, preferably a nucleoside or nucleoside analog.

In other embodiments, the compound has a structure represented by Formula (II):

or a pharmaceutically acceptable salt thereof, wherein
W is H or phosphate;
Y is —NH— or —O—, and
$L^2$ is wherein $L^{2a}$ is alkylene; each $R^1$ is independently $O^-$, O-alkyl, NH-alkyl, or alkyl; Z is O or NH; n is 0 or 1; * is the point of attachment to the oxygen atom; and ** is the point of attachment to D, or
Y and $L^2$ are absent; and
D is an antiviral moiety, preferably a nucleoside or nucleoside analog.

In certain embodiments, the disclosure relates to any of the foregoing compounds wherein D is a nucleoside or nucleoside analog of the formula D1-D2, where D1 is a sugar or sugar analog, and D2 is a nucleobase or nucleobase analog. In some embodiments, D is a viral RNA chain terminator.

In some embodiments, the disclosure relates to any of the foregoing compounds wherein $D^2$ is represented by Formula (III)

(III)

wherein
each $X^1$, $X^2$, $X^3$, $Y^1$, and $Y^2$ is independently $CR^{10}$ or N, provided that at least one of $X^1$, $X^2$, and $X^3$ is $CR^{10}$, and at least one of $Y^1$, $Y^2$, and $X^3$ is $CR^{10}$;

$R^4$ is halogen, $NR^{11}R^{12}$, $N(R^{11})OR^{13}$, $NR^{11}NR^{11}R^{12}$, $NR^{11}R^{15}$, $N_3$, NO, $NO_2$, CHO, CN, —CH(=NR$^1$), —CH=NNHR$^{11}$, —CH=N(OR$^{13}$), —C(=O)NR$^{11}R^{12}$, —C(=S)NR$^{11}R^{12}$, —C(=O)OR$^{13}$, (C1-6)alkyl, (C2-6)alkenyl, (C2-6)alkynyl, aryl, heteroaryl, —C(=O)(C1-6)alkyl, —S(O)$_n$(C1-6)alkyl, aryl(C1-6)alkyl, $OR^{13}$, $OR^{15}$, $SR^{14}$, or $SR^{15}$;

each $R^5$ and $R^{10}$ is independently H, halogen, $NR^{11}R^{12}$, $N(R^{11})OR^{13}$, $NR^{11}NR^{11}R^{12}$, $NR^{11}R^{15}$, $N_3$, NO, $N_{02}$, CHO, CN, —CH(=NR$^1$), —CH=NNHR$^{11}$, —CH=N(OR$^{13}$), —C(=O)NR$_{11}R_{12}$, —C(=S)NR$^{11}R^{12}$, —C(=O)OR$^{13}$, $R^{11}$, $OR^{13}$, $OR^{15}$, $SR^{14}$, or $SR^{15}$;

each $R^{11}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{11}$ is the point of attachment to $D^1$, and each $R^{12}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{11}$ and $R^{12}$ taken together with a nitrogen to which they are both attached form a 3- to 7-membered heterocyclic ring;

each $R^{13}$ and $R^{14}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{13}$ or $R^{14}$ is the point of attachment to $D^1$;

$R^{15}$ is the point of attachment of D to $L^1$ or $L^2$; and
each n is independently 0, 1, or 2;
or $D^2$ is represented by Formula (IV)

(IV)

wherein
$R^6$ is halogen, $NR^{11}R^{12}$, $N(R^{11})OR^{13}$, $NR^{11}NR^{11}R^{12}$, $NR^{11}R^{15}$, $N_3$, NO, $N_{02}$, CHO, CN, —CH(=NR$^{11}$), —CH=NNHR$^{11}$, —CH=N(OR$^{13}$), —C(=O)NR$^{11}R^{12}$, —C(=S)NR$^{11}R^{12}$, —C(=O)OR$^{13}$, (C1-6)alkyl, (C2-6)alkenyl, (C2-6)alkynyl, aryl, heteroaryl, —C(=O)(C1-6)alkyl, —S(O)$_n$(C1-6)alkyl, aryl(C1-6)alkyl, $OR^{13}$, $OR^{15}$, $SR^{14}$, or $SR^{15}$, or two geminal occurrences of $R^6$ taken together form a carbonyl; and $R^7$ is H, halogen, $NR^{11}R^{12}$, $N(R^{11})OR^{13}$, $NR^{11}NR^{11}R^{12}$, $NR^{11}R^{15}$, $N_3$, NO, $N_{02}$, CHO, CN, —CH(=NR$^D$), —CH=NNHR$^{11}$, —CH=N(OR$^{13}$), —C(=O)NR$_{11}R_{12}$, —C(=S)NR$^{11}R^{12}$, —C(=O)OR$^{13}$, $R^{11}$, $OR^{13}$, $OR^{15}$, $SR^{14}$, or $SR^{15}$, or two geminal occurrences of $R^7$ taken together form a carbonyl.

In preferred embodiments, $D^1$ is

In some preferred embodiments, $D^2$ is and $R^{11}$ is the point of attachment to $D^1$.

In some embodiments, the compound has the structure or a pharmaceutically acceptable salt thereof.

In other embodiments, the compound has the structure or a pharmaceutically acceptable salt thereof.

In further embodiments, the compound has the structure or a pharmaceutically acceptable salt thereof.

In still further embodiments, the compound has the structure or a pharmaceutically acceptable salt thereof.

In some embodiments, the disclosure relates to any of the foregoing compounds wherein D is an antiviral moiety selected from abacavir, acyclovir, adefovir, amantadine, amprenavir, atazanavir, baloxavir marboxil, boceprevir, cidofovir, cobicistat, daclatasvir, darunavir, delavirdine, descovy, didanosine, docosanol, dolutegravir, doravirine, edoxudine, efavirenz, elvitegravir, emtricitabine, enfuvirtide, entecavir, etravirine, favipiravir, favipiravir riboside, famciclovir, fosamprenavir, ganciclovir, ibacitabine, idoxuridine, imiquimod, indinavir, lamivudine, letermovir, lopinavir, loviride, maraviroc, methisazone, moroxydine, nelfinavir, nevirapine, nitazoxanide, norvir, oseltamivir, penciclovir, peramivir, penciclovir, peramivir, pleconaril, podophyllotoxin, raltegravir, remdesivir, GS-441524, GS-443902, de-phospho-GS-441524, ribavirin, rilpivirine, rimantadine, ritonavir, saquinavir, simeprevir, sofosbuvir, stavudine, taribavirin, telaprevir, telbivudine, tenofovir alafenamide, tenofovir disoproxil, tipranavir, trifluridine, tromantadine, umifenovir, valaciclovir, valganciclovir, vicriviroc, vidarabine, zalcitabine, zanamivir, zidovudine, preferably ribavirin, wherein the antiviral moiety differs from the named antiviral drug by a covalent bond as shown in Formula I or II.

The present disclosure also relates to pharmaceutical compositions comprising such compounds and/or pharmaceutically acceptable salts thereof, along with one or more pharmaceutically acceptable excipients.

Additionally, the disclosure relates to methods of treating a viral infection in a subject, comprising administering such compounds, pharmaceutically acceptable salts, and/or pharmaceutical compositions, to the subject. In preferred embodiments, the viral infection is COVID-19.

Also included are methods of increasing NAD levels in a subject, comprising administering such compounds, pharmaceutically acceptable salts, and/or pharmaceutical compositions, to the subject.

DETAILED DESCRIPTION

Definitions

Unless defined otherwise, all technical and scientific terms used herein have the meaning commonly understood by a person skilled in the art of the present disclosure. As used herein, the following terms have the meanings ascribed to them below, unless specified otherwise.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The phrase "antiviral moiety" refers to a class of medications used for treating viral infections, often by inhibiting development of the virus, or at times by interfering with binding of the virus to a host cell. An antiviral moiety may differ from a named antiviral drug by the existence of a covalent bond to another moiety, forming a compound according to Formula I or II as described herein.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$," when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group wherein each $R^{30}$ independently represents a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group wherein $R^{32}$ and $R^{33}$ independently represent hydrogen or a hydrocarbyl group, such as an alkyl group, or $R^{32}$ and $R^{33}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{34}$, wherein $R^{34}$ represents a hydrocarbyl group.

The term "carboxy", as used herein, refers to a group represented by the formula —$CO_2H$.

The term "ester", as used herein, refers to a group —$C(O)OR^{35}$ wherein $R^{35}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae wherein $R^{36}$ and $R^{37}$ independently represent hydrogen or hydrocarbyl, such as alkyl, or $R^{36}$ and $R^{37}$ taken together with the intervening atom(s) complete a heterocycle having from 4 to 8 atoms in the ring structure.

The term "sulfoxide" is art-recognized and refers to the group —S(O)—$R^{38}$, wherein $R^{38}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^{39}$, wherein $R^{39}$ represents a hydrocarbyl.

The term "thioalkyl", as used herein, refers to an alkyl group substituted with a thiol group.

The term "thioester", as used herein, refers to a group —C(O)S$R^{40}$ or —SC(O)$R^{40}$ wherein $R^{10}$ represents a hydrocarbyl.

The term "thioether", as used herein, is equivalent to an ether, wherein the oxygen is replaced with a sulfur.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "metabolite," as described herein, refers to a compound produced in vivo after administration to a subject.

The term "salts," as described herein, refers to a compound wherein the parent compound is altered by converting an existing acid or base moiety to its salt form (e.g., by reacting a free base group with a suitable organic acid). It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR_{4-g}^+$, in which R is a $C_{1-3}$ alkyl and g is a number selected from 0, 1, 2, 3, or 4. It should be understood that all references to pharmaceutically acceptable salts include solvent addition forms (solvates) or crystalline solids as defined herein, of the same acid addition salt.

The present disclosure also includes useful forms of the compounds of the present disclosure, such as metabolites, solvates, prodrugs, salts, in particular pharmaceutically acceptable salts, and/or co-precipitates.

The compounds of the present disclosure can exist as solvates, wherein the compounds of the present disclosure form a crystal that contains molecules of polar solvents, such as water, methanol or ethanol, for example, as structural element of the crystal lattice of the compounds. The molecules of polar solvents may be present in a stoichiometric or non-stoichiometric ratio with the molecules of the compound. In the case of stoichiometric solvates, e.g., hemi-, (semi-), mono-, sesqui-, di-, tri-, tetra-, penta- etc. solvates, respectively, are possible. The present disclosure includes all such solvates.

Further, it is possible for the compounds of the present disclosure to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present disclosure.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

As used herein, a therapeutic that "prevents" a disorder or condition refers to a compound and/or crystalline solid thereof that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "preparation" or "dosage form" is intended to include both solid and liquid formulations of the active compound and/or crystalline solid thereof, and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution;

(19) ethyl alcohol; (20) phosphate buffer solutions; and (21) other non-toxic compatible substances employed in pharmaceutical formulations.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

It is to be understood that wherever values and ranges are provided herein, all values and ranges encompassed by these values and ranges are meant to be encompassed within the scope of the present disclosure. Moreover, all values that fall within these ranges, as well as the upper or lower limits of a range of values, are also contemplated by the present application.

Compounds

The present disclosure relates to anti-viral compounds comprising an NAD-boosting moiety linked to an antiviral moiety, and compositions and methods of use thereof. Without wishing to be bound by theory, compounds according to Formula I and II may be considered prodrugs of antiviral drugs, where the compounds include an NMN (nicotinamide mononucleotide) or nicotinic acid mononucleotide moiety coupled with an antiviral moiety via a linker, which upon cleavage of the linker, releases the antiviral moiety and the NMN or nicotinic acid mononucleotide moiety.

In certain embodiments, the disclosure relates to a compound having a structure represented by Formula (I):

(I)

or a pharmaceutically acceptable salt thereof, wherein
X is $NH_2$ or OH;
$L^1$ is a linker such as wherein each $R^1$ is independently OH, $O^-$, O-alkyl, NH-alkyl, or alkyl; Z is O or NH; n is 0 or 1; * is the point of attachment to the oxygen atom; and ** is the point of attachment to D; and
D is an antiviral moiety, preferably a nucleoside or nucleoside analog.

In certain embodiments, the disclosure relates to any of the compounds described herein, wherein X is OH. In other embodiments, the disclosure relates to any of the compounds described herein, wherein X is $NH_2$.

In some embodiments, the disclosure relates to any of the compounds described herein, wherein $R^1$ is OH. In some embodiments, the disclosure relates to any of the compounds described herein, wherein $R^1$ is $O^-$.

In certain embodiments, the disclosure relates to any of the compounds described herein, wherein Z is O.

In some embodiments, the disclosure relates to any of the compounds described herein, wherein n is 1. In other embodiments, the disclosure relates to any of the compounds described herein, wherein n is 0.

In additional embodiments, the disclosure relates to a compound having a structure represented by Formula (II):

(II)

or a pharmaceutically acceptable salt thereof, wherein
W is H or phosphate;
Y is —NH— or —O—, and
$L^2$ is a linker, such as wherein $L^{2a}$ is alkylene; each $R^1$ is independently OH, O-, O-alkyl, NH-alkyl, or alkyl; Z is O or NH; n is 0 or 1; * is the point of attachment to the oxygen atom; and ** is the point of attachment to D, or
Y and $L^2$ are absent; and
D is an antiviral moiety, preferably a nucleoside or nucleoside analog.

In some embodiments, the disclosure relates to any of the compounds described herein, wherein W is H. In other embodiments, the disclosure relates to any of the compounds described herein, wherein W is phosphate.

In certain embodiments, the disclosure relates to any of the compounds described herein, wherein Y is —O—. In other embodiments, the disclosure relates to any of the compounds described herein, wherein Y is —HN—.

In some embodiments, the disclosure relates to any of the compounds described herein, wherein $L^2a$ is (C1-3)alkylene, preferably, $L^2a$ is C3 alkylene.

In some embodiments, the disclosure relates to any of the compounds described herein, wherein each $R^1$ is independently OH, O-alkyl, NH-alkyl, or alkyl; Z is O or NH; n is 0 or 1. In certain embodiments, the disclosure relates to any of the compounds described herein, wherein $R^1$ is independently O⁻, O-alkyl, NH-alkyl, or alkyl; Z is O or NH; n is 0 or 1. In some such embodiments, the disclosure relates to any of the compounds described herein, wherein $R^1$ is OH.

In certain embodiments, the disclosure relates to any of the compounds described herein, wherein Z is O.

In some embodiments, the disclosure relates to any of the compounds described herein, wherein n is 1. In other embodiments, the disclosure relates to any of the compounds described herein, wherein n is 0.

In certain embodiments, the disclosure relates to any of the compounds described herein, wherein Y and $L^2$ are absent.

In some embodiments, the disclosure relates to any of the compounds described herein, wherein D is a nucleoside or nucleoside analog of the formula $D^1$-$D^2$, where $D^1$ is a sugar or sugar analog, and $D^2$ is a nucleobase or nucleobase analog. In preferred embodiments, the disclosure relates to any of the compounds described herein, wherein D is a viral RNA chain terminator.

In certain embodiments, the disclosure relates to any of the compounds described herein, wherein $D^1$ is a sugar. For example, in some embodiments, $D^1$ is an aminosugar. In other embodiments, $D^1$ is an iminosugar. In still other embodiments, $D^1$ is a furanose. In certain embodiments, $D^1$ is a ribose. For example, in some embodiments, $D^1$ is a 1-deoxyribose. In other embodiments, $D^1$ is a 1,2-dideoxyribose.

In some embodiments, the disclosure relates to any of the compounds described herein, wherein $D^1$ is substituted by one or more $R^2$, wherein each $R^2$ is independently (C1-3) alkyl, fluoro, or cyano, preferably cyano.

In certain embodiments, the disclosure relates to any of the compounds described herein, wherein $D^1$ is substituted by $R^2$ at the C1' position. In some embodiments, the disclosure relates to any of the compounds described herein, wherein $D^1$ is substituted by $R^2$ at the C2' position.

In certain embodiments, the disclosure relates to any of the compounds described herein, wherein one or more oxygen atoms of $D^1$ is bonded to a group —C(O)$R^3$, where each $R^3$ is independently (C1-6)alkyl, for example methyl.

In some embodiments, the disclosure relates to any of the compounds described herein, wherein $D^1$ is attached to $D^2$ at the C1' position.

In some embodiments, the disclosure relates to any of the compounds described herein, wherein $D^1$ is attached at the C5' position to $L^1$ or $L^2$.

In preferred embodiments, the disclosure relates to any of the compounds described herein, wherein $D^1$ is In certain embodiments, the disclosure relates to any of the compounds described herein, wherein $D^2$ is a purine or purine analog. In certain embodiments, the disclosure relates to any of the compounds described herein, wherein D2 is a pyrimidine or pyrimidine analog.

In certain embodiments, the disclosure relates to any of the compounds described herein, wherein $D^2$ is represented by Formula (III)

(III)

wherein
each $X^1$, $X^2$, $X^3$, $Y^1$, and $Y^2$ is independently $CR^{10}$ or N, provided that at least one of $X^1$, $X^2$, and $X^3$ is $CR^{10}$, and at least one of $Y^1$, $Y^2$, and $X^3$ is $CR^{10}$;

$R^4$ is halogen, $NR^{11}R^{12}$, $N(R^{11})OR^{13}$, $NR^{11}NR^{11}R^{12}$, $NR^{11}R^{15}$, $N_3$, NO, $NO_2$, CHO, CN, —CH(=$NR^{11}$), —CH=$NNHR^{11}$, —CH=N(OR$^{13}$), —C(=O)NR$^{11}$R$^{12}$, —C(=S)NR$^{11}$R$^{12}$, —C(=O)OR$^{13}$, (C1-6) alkyl, (C2-6)alkenyl, (C2-6)alkynyl, aryl, heteroaryl, —C(=O)(C1-6)alkyl, —S(O)$_n$(C1-6)alkyl, aryl(C1-6) alkyl, OR$^{13}$, OR$^{15}$, SR$^{14}$, or SR$^{15}$;

each $R^5$ and $R^{10}$ is independently H, halogen, $NR^{11}R^{12}$, $N(R^{11})OR^{13}$, $NR^{11}NR^{11}R^{12}$, $NR^{11}R^{15}$, $N_3$, NO, $NO_2$, CHO, CN, —CH(=$NR^1$), —CH=$NNHR^{11}$, —CH=N(OR$^{13}$), —C(=O)NR$_{11}$R$_{12}$, —C(=S)NR$^{11}$R$^{12}$, —C(=O)OR$^{13}$, R$^{11}$, OR$^{13}$, OR$^{15}$, SR$^{14}$, or SR$^{15}$;

each $R^{11}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{11}$ is the point of attachment to $D^1$, and each $R^{12}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{11}$ and $R^{12}$ taken together with a nitrogen to which they are both attached form a 3- to 7-membered heterocyclic ring;

each $R^{13}$ and $R^{14}$ is independently H, (C1-6)alkyl, (C2-6)alkenyl, (C2-6)alkynyl, aryl, heteroaryl, —C(=O)(C1-6)alkyl, —S(O)$_n$(C1-6)alkyl, or aryl(C1-6)alkyl, or $R^{13}$ or $R^{14}$ is the point of attachment to $D^1$;

$R^{15}$ is the point of attachment of D to $L^1$ or $L^2$; and each n is independently 0, 1, or 2;

or $D^2$ is represented by Formula (IV)

(IV)

wherein
$R^6$ is halogen, $NR^{11}R^{12}$, $N(R^{11})OR^{13}$, $NR^{11}NR^{11}R^{12}$, $NR^{11}R^{15}$, $N_3$, NO, $N_{02}$, CHO, CN, —CH(=$NR^{11}$), —CH=$NNHR^{11}$, —CH=N(OR$^{13}$), —C(=O) NR$^{11}$R$^{12}$, —C(=S)NR$^{11}$R$^{12}$, —C(=O)OR$^{13}$, (C1-6) alkyl, (C2-6)alkenyl, (C2-6)alkynyl, aryl, heteroaryl, —C(=O)(C1-6)alkyl, —S(O)$_n$(C1-6)alkyl, aryl(C1-6) alkyl, OR$^{13}$, OR$^{15}$, SR$^{14}$, or SR$^{15}$, or two geminal occurrences of $R^6$ taken together form a carbonyl; and $R^7$ is H, halogen, $NR^{11}R^{12}$, $N(R^{11})OR^{13}$, $NR^{11}NR^{11}R^{12}$, $NR^{11}R^{15}$, $N_3$, NO, $NO_2$, CHO, CN, —CH(=$NR^{11}$), —CH=$NNHR^{11}$, —CH=N(OR$^{13}$), —C(=O)

NR[11]R[12], —C(=S)NR[11]R[12], —C(=O)OR[13], R[11], OR[13], OR[15], SR[14], or SR[15], or two geminal occurrences of R[7] taken together form a carbonyl.

In certain embodiments, the disclosure relates to any of the compounds described herein, wherein D[2] is of the formula (III). In certain embodiments, the disclosure relates to any of the compounds described herein, wherein D2 is of the formula (IV).

In some embodiments, the disclosure relates to any of the compounds described herein, wherein X[1], X[2], and X[3] are CR[10]. In other embodiments, the disclosure relates to any of the compounds described herein, wherein X[1] and X[2] are CH. In certain embodiments, the disclosure relates to any of the compounds described herein, wherein X[3] is CR[11], and R[11] is the point of attachment to D[1].

In certain embodiments, the disclosure relates to any of the compounds described herein, wherein Y[1] and Y[2] are N.

In some embodiments, the disclosure relates to any of the compounds described herein, wherein R[4] is NR[11]R[12]. In other embodiments, the disclosure relates to any of the compounds described herein, wherein N(R[11])OR[13]. In certain embodiments, the disclosure relates to any of the compounds described herein, wherein R[4] is NR[11]R[12]. In other embodiments, the disclosure relates to any of the compounds described herein, wherein R[4] is NR[11]R[15]. In some embodiments, the disclosure relates to any of the compounds described herein, wherein R[4] is NH$_2$.

In certain embodiments, the disclosure relates to any of the compounds described herein, wherein R[5] is H.

In preferred embodiments, the disclosure relates to any of the compounds described herein, wherein D[2] is and R[11] is the point of attachment to D[1].

In some embodiments, the disclosure relates to any of the compounds described herein, wherein R[6] is NR[11]R[12]. In other embodiments, the disclosure relates to any of the compounds described herein, wherein R[6] is N(R[11])OR[13]. In certain embodiments, the disclosure relates to any of the compounds described herein, wherein R[6] is NR[11]R[12]. In some embodiments, the disclosure relates to any of the compounds described herein, wherein two geminal occurrences of R[6] taken together form a carbonyl.

In certain embodiments, the disclosure relates to any of the compounds described herein, wherein R[7] is H. In other embodiments, the disclosure relates to any of the compounds described herein, wherein two geminal occurrences of R[7] taken together form a carbonyl.

In certain embodiments, the disclosure relates to any of the compounds described herein, wherein each R[11] is independently H, (C1-6)alkyl, or the point of attachment to D[1].

In certain embodiments, the disclosure relates to any of the compounds described herein, wherein each R[12], R[13], and R[14] is independently H or (C1-6)alkyl.

In some embodiments, the disclosure relates to any of the compounds described herein, wherein D[2] is a purine. In other embodiments, the disclosure relates to any of the compounds described herein, wherein D[2] is a pyrimidine.

In some embodiments, the disclosure relates to any of the compounds described herein, wherein D is In some embodiments, the disclosure relates to any of the compounds described herein wherein D is In certain embodiments, the disclosure relates to a compound having the structure or a pharmaceutically acceptable salt thereof. In some embodiments, the pharmaceutically acceptable salt is formed with a cation having the opposite charge as the phosphate group.

In certain embodiments the disclosure relates to a compound having the structure or a pharmaceutically acceptable salt thereof.

In other embodiments, the disclosure relates to a compound having the structure or a pharmaceutically acceptable salt thereof.

In still other embodiments, the disclosure relates to a compound having the structure or a pharmaceutically acceptable salt thereof.

In further embodiments, the disclosure relates to a compound having the structure or a pharmaceutically acceptable salt thereof. In some embodiments, the pharmaceutically acceptable salt is formed with a cation having the opposite charge as the phosphate group.

In still further embodiments, the disclosure relates to a compound having the structure or a pharmaceutically acceptable salt thereof.

In some embodiments, the disclosure relates to any of the foregoing compounds wherein D is an antiviral moiety selected from abacavir, acyclovir, adefovir, amantadine, amprenavir, atazanavir, baloxavir marboxil, boceprevir, cidofovir, cobicistat, daclatasvir, darunavir, delavirdine, descovy, didanosine, docosanol, dolutegravir, doravirine, edoxudine, efavirenz, elvitegravir, emtricitabine, enfuvirtide, entecavir, etravirine, favipiravir, favipiravir riboside, famciclovir, fosamprenavir, ganciclovir, ibacitabine, idoxuridine, imiquimod, indinavir, lamivudine, letermovir, lopinavir, loviride, maraviroc, methisazone, moroxydine, nelfinavir, nevirapine, nitazoxanide, norvir, oseltamivir, penciclovir, peramivir, penciclovir, peramivir, pleconaril, podophyllotoxin, raltegravir, remdesivir, GS-441524, GS-443902, de-phospho-GS-441524, ribavirin, rilpivirine, rimantadine, ritonavir, saquinavir, simeprevir, sofosbuvir, stavudine, taribavirin, telaprevir, telbivudine, tenofovir alafenamide, tenofovir disoproxil, tipranavir, trifluridine, tromantadine, umifenovir, valaciclovir, valganciclovir, vicriviroc, vidarabine, zalcitabine, zanamivir, zidovudine, preferably ribavirin, wherein the antiviral moiety differs from the named antiviral drug by a covalent bond as shown in Formula I or II.

It will be apparent that the compounds may exist in various protonation states, depending on, among other things, the pH of their environment. In various pH environments, the compounds exist as zwitterions, or internal salts, as drawn herein.

In various embodiments, the compounds are one or more salts, wherein said salts are formed with a cation selected from $H^+$, $Li^+$, $Na^+$, $K^+$, $Mg^{2+}$, and $Ca^{2+}$ and/or said salts are formed with an anion selected from acetate, trifluoromethansulfonate (triflate), halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$, and mixtures thereof. In various embodiments, the compound is a zwitterion.

The present disclosure includes the use of pharmaceutically acceptable salts of compounds of the disclosure and/or crystalline solids thereof. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts.

In certain embodiments, the compound is a salt with an anion selected from acetate, triflate, halide, trifluoroacetate, or formate. In other embodiments, if the disclosed compound is in contact with a media, e.g., aqueous media, the anion can be selected from, for example, $OH^-$, $H_2PO_4^-$, $HPO_4^{2-}$, $HSO_4^-$, $SO_4^{2-}$, $NO_3^-$, $HCO_3^-$, and $CO_3^{2-}$.

In some embodiments, the disclosed compounds are in the form of a negatively charged phosphate, which may form a salt with any suitable cation. The cation can alter as the compound is isolated or transferred into media with different anionic species. For example, a disclosed compound may be in the form of a phosphate salt that is a pharmaceutically acceptable salt as described herein. In certain embodiments, the cation can be selected from $Li^+$, $Na^+$, $K^+$, $Mg^{2+}$, and $Ca^{2+}$.

Compositions and Pharmaceutical Formulations

While it is possible for the active ingredients to be administered alone, it may be preferable to present them as pharmaceutical formulations. The formulations, both for veterinary and for human use, of the present disclosure comprise at least one active ingredient, as above defined, together with one or more acceptable carriers therefor and optionally other therapeutic ingredients. In some embodiments, the amount of the compound of the disclosure in the composition is about 0.0010% by weight to about 90% by weight, about 0.01% by weight to about 50% by weight, or about 0.10% by weight to about 20% by weight of the composition.

Although the dosage will vary depending on the symptoms, age and body weight of the patient, the nature and severity of the disorder to be treated or prevented, the route of administration and the form of the drug, in general, a daily dosage of from 0.01 to 3000 mg per day of the compound is recommended for an adult human patient, and this may be administered in a single dose or in divided doses. Doses may range are from about 0.01 to about 50 mg/kg of body weight per day, given in 1 single or 2-4 divided doses. In certain embodiments, the compounds described herein are administered in an amount from about 1 to about 3000 mg per day, from about 100 to about 1000 mg per day, or from about 250 to about 750 mg per day. If desired, the effective daily dose of the active compound may be administered as one, two, three, four, five, six or more sub-doses administered separately at appropriate intervals throughout the day, optionally, in unit dosage forms. In some embodiments, the compounds described herein are administered one, two, three, four, five, six or more times per day. The amount of active ingredient which can be combined with a carrier material to produce a single dosage form will generally be that amount of the compound which produces a therapeutic effect.

The compounds of this disclosure are formulated with conventional carriers and excipients, which can be selected in accord with ordinary practice. All formulations will optionally contain excipients such as those set forth in the "Handbook of Pharmaceutical Excipients" (1986). Suitable excipients are also listed in the US Food and Drug Administration Inactive Ingredients Database. Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations can range from about 3 to about 11, but is ordinarily about 7 to about 10.

Pharmaceutical formulations according to the present disclosure comprise a compound according to the this disclosure together with one or more pharmaceutically acceptable carriers or excipients and optionally other therapeutic agents. Pharmaceutical formulations containing the active ingredient may be in any form suitable for the intended method of administration. When intended for oral use for example, tablets, pills, capsules, caplets, sachets, a pastille, a lozenge, a chewable, troches, lozenges, aqueous or oil suspensions, dispersible powders or granules, emulsions, hard or soft capsules, syrups or elixirs may be prepared. In certain embodiments, the composition is in the form of a tablet. In other embodiments, the composition is in a form of a hard or soft gelatin capsule. Formulations of the present disclosure suitable for oral administration may be presented as discrete units such as capsules, cachets or tablets, each containing a predetermined amount of the active ingredient as a powder or granules. The active ingredient may also be administered as a bolus, electuary or paste.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

A tablet is made by compression or molding, optionally with one or more accessory ingredients. Tablets can contain excipients, glidants, fillers, binders and the like. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the present disclosure contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Liquid formulations may also include eye drops or other forms of delivery to the surface of the eye or adjacent locations such as tear ducts. Liquid formulations may include intravenous formulations, excipients, and carriers such as saline solution, or buffered solution, and the packaging or containers for such formulations, for injection or infusion or the like.

Dispersible powders and granules of the present disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In some embodiments, the pharmaceutically acceptable excipient is selected from an anti-adherent, binder, coating, dye, disintegrant, flavoring agent, glidant, lubricant, preservative, sorbent, sweetener, syrups, elixirs, dispersant, diluent, filler, granulating agent, coating agent, wax, suspending agent, wetting agent, thickener and vehicle and combinations thereof. In some embodiments, the excipient is a solid excipient.

In some embodiments, the pharmaceutically acceptable excipient is present in an amount of at least about 5% by weight, at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, or at least about 60% by weight of the composition. In some embodiments, the pharmaceutically acceptable excipient is present in an amount of at least about 20% by weight, at least about 25% by weight, at least about 30% by weight, at least about 35% by weight, or at least about 40% by weight, preferably at least about 30% by weight of the composition. In other embodiments, the pharmaceutically acceptable excipient is present in an amount of at least about 50% by weight of the composition.

It should be understood that in addition to the ingredients particularly mentioned above, the formulations of this disclosure may include other agents conventional in the art having regard to the type of formulation in question, for example, those suitable for oral administration may include flavoring agents.

In some embodiments, the compound is the sole active pharmaceutical ingredient in the composition. Alternatively, the compound solid is formulated in a composition with one or more additional active pharmaceutical ingredients. When formulated as the sole active pharmaceutical ingredient, the compound may be administered individually, or as part of a regimen with one or more separately formulated active pharmaceutical ingredients.

Diseases, Disorders and Conditions, and Methods of Treatment

Provided herein are methods for using the disclosed compounds and pharmaceutical compositions thereof. The disclosed compounds and pharmaceutical compositions thereof can be useful for a variety of therapeutic applications including, for example, treating and/or reducing a wide variety of diseases and disorders including, for example, viral infection. Provided herein are methods of treating viral infection in a subject in need thereof, the method comprising administering a composition as described herein to the subject. In various embodiments, the viral infection is infection with a coronavirus. In various embodiments, the viral infection is infections with SARS or MERS. In various embodiments, the viral infection is infections with COVID-19, also known as SARS-CoV-2, and variants thereof. The methods comprise administering to a subject in need thereof a disclosed compound and/or pharmaceutical composition thereof. In various embodiments, the composition is administered orally, alternately in an out-patient setting, optionally by the subject in need of treatment. An aspect of the present disclosure provides methods of increasing NAD levels in a subject in need thereof, such methods comprising administering a composition as described herein to the subject. In various embodiments, the composition is administered orally. An aspect of the present disclosure provides methods of administering a composition to a subject in need thereof to achieve both an antiviral effect while also increasing NAD levels.

The disclosed compounds and pharmaceutical compositions thereof can also be used to treat a disease or disorder associated with inflammation related to viral infection. Exemplary inflammatory conditions include, for example, multiple sclerosis, rheumatoid arthritis, psoriatic arthritis, degenerative joint disease, spondyloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatitis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

The disclosed compounds and pharmaceutical compositions thereof can also be administered to a subject suffering from an acute disease related to viral infection, e.g., damage to an organ or tissue, e.g., a subject suffering from stroke or myocardial infarction, or a subject undergoing transplant of a solid organ such as the liver or kidney. In some embodiments, the compounds and pharmaceutical compositions thereof may be administered to a subject suffering from acute kidney injury (AKI), also known as acute renal failure (ARF), related to viral infection. Subjects suffering from or at risk of suffering from AKI may be screened for kidney function, for example by testing for abnormal levels of serum creatinine. Subjects may be treated prophylactically or in response to acute kidney injury, such as stage 1 AKI. Subjects undergoing solid organ transplant may be treated prophylactically, or post-transplant, or the individual organs may be treated outside the body prior to transplant, as a form of organ preservation. Subjects undergoing surgery other than organ transplant, such as biopsy or resection or repair of traumatic injury, may be treated prophylactically, or post-surgery.

The disclosed compounds and pharmaceutical compositions thereof may also be used for a subject suffering from or likely to suffer from chronic damage or chronic disease in a solid organ, such as the kidney or liver, related to viral infection. In some embodiments, pharmaceutical compositions may be administered to a subject suffering from chronic kidney disease, such as end stage renal failure, or such as nephropathy, or such as diabetic nephropathy. In some embodiments, pharmaceutical compositions thereof may be administered to a subject suffering from chronic liver disease, such as chronic infection, cirrhosis, or liver cancer, in order to repair or limit further damage to the liver. In some embodiments, pharmaceutical compositions may be administered to repair an alcoholic's liver, or to stabilize or repair damage from non-alcoholic steatohepatitis (NASH) or non-alcoholic fatty liver disease (NAFLD).

In other embodiments, provided herein is a method for treating a cardiovascular disease related to viral infection by administering to a subject in need thereof a disclosed compound, and/or a pharmaceutical composition thereof. Cardiovascular diseases that can be treated using the disclosed compounds and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The disclosed compounds and pharmaceutical compositions thereof may also be used for increasing HDL levels in plasma of an individual.

Viral infections such as herpes, HIV, adenovirus, and HTLV-1 associated malignant and benign disorders can also be treated by administration of the disclosed compounds and pharmaceutical compositions thereof.

In some embodiments, the disclosed compounds and pharmaceutical compositions thereof can be used to treat patients suffering from infectious diseases—such as COVID-19 and other viral infections—including those experiencing symptoms such as cytokine release syndrome (cytokine storm). In some embodiments, the compounds and pharmaceutical compositions thereof alleviate or prevent cytokine storm without necessarily treating the underlying viral infection (e.g., COVID-19). Cytokine release syndrome is an acute systemic inflammatory syndrome that can arise from a variety of causes. In particular, cytokine storms have been described in COVID-19 as well as other severe viral syndromes (SARS, MERS). A subset of patients exhibits notably elevated cytokines, and severe patients can also exhibit much higher levels of IL6, CRP, ferritin, D-dimer, and other markers, as well as lymphopenia (reduced count of CD4+ and CD8+ T cells). For example, in one report, a D-dimer level on admission of >2.0 ug/ml identified a subset of patients likely to die (12/67>=2.0 vs 1/267<2.0, sensitivity 92.3%, specificity 83.3%) ("D-dimer levels on admission to predict in-hospital mortality in patients with Covid-19." Zhang L, Yan X, Fan Q, et al. *J Thromb Haemost*. 2020 Apr. 19). NAD modulates the NLRP3 inflammasome release of IL-IB, by which it may modulate the cytokine storm. NAD levels are known to decline with age, which may also contribute to worse outcomes for older COVID-19 patients. An aspect of the present disclosure provides a method of treating COVID-19 in a human patient comprising administering thee disclosed compounds and pharmaceutical compositions thereof to said patient.

In some embodiments, the disclosed compounds and pharmaceutical compositions thereof can be used to treat patients suffering from neurodegenerative diseases related to viral infection, and injury to the central nervous system (CNS) or peripheral nervous system (PNS). Examples of neurodegenerative diseases include, but are not limited to, ataxia, Alzheimer's disease (AD), a dementia other than Alzheimer's Disease, Parkinson's disease (PD), Huntington disease (HD), amyotrophic lateral sclerosis (ALS; Lou Gehrig's disease), diffuse Lewy body disease, chorea-acanthocytosis, primary lateral sclerosis, multiple sclerosis (MS), ocular diseases (ocular neuritis), spinal muscle atrophy, chemotherapy-induced neuropathies (e.g., from vincristine, paclitaxel, bortezomib), diabetes-induced neuropathies, and Friedreich's ataxia.

In some embodiments, the disclosed compounds and pharmaceutical compositions thereof may be used for treatment of skeletomuscle disorders, muscular disorders, and conditions including muscle loss, atrophy, and sarcopenia, related to viral infection.

In addition, methods as described herein include methods of modulating the level of NAD in at least one tissue or cell type in a mixture of tissues or cell types, such methods comprising targeted delivery of a compound or composition as described herein to the desired tissue or cell type. In various embodiments, the targeted delivery is non-systemic.

In some embodiments, the delivery of an antiviral drug is improved by the use of an NAD-boosting moiety covalently linked to a precursor of the antiviral drug, with the intention of releasing the antiviral drug upon cleavage of the linker in vivo following administration to a subject in need of an antiviral drug. In various embodiments, a drug that otherwise requires parenteral injection or administration via a non-oral route can be administered orally when administered as a compound according to Formula I or II.

The invention now being generally described, it will be more readily understood by reference to the following examples, which are included merely for purposes of illustration of certain aspects and embodiments of the present invention, and are not intended to limit the invention.

EXAMPLES

Example 1a: Synthetic Scheme

Compound 1 (((2R,3S,4R,5R)-5-(4-aminopyrrolo[2,1-f][1,2,4]triazin-7-yl)-5-cyano-3,4-dihydroxytetrahydrofuran-2-yl)methyl (((2R,3S,4R,5R)-5-(3-carboxy-1λ⁴-pyridin-1-yl)-3,4-dihydroxytetrahydrofuran-2-yl)methyl) phosphate)

Compound 2 (((2R,3S,4R,5R)-5-(3-((((2R,3S,4R,5R)-5-(4-aminopyrrolo[2,1-f][1,2,4]triazin-7-yl)-5-cyano-3,4-dihydroxytetrahydrofuran-2-yl)methoxy)carbonyl)-1λ⁴-pyridin-1-yl)-3,4-dihydroxytetrahydrofuran-2-yl)methyl hydrogen phosphate)

Experimental Procedure

Phosphorus oxychloride (0.33 mL, 3.6 mmol, 1.2 equiv.) was added dropwise to a stirred solution of NAR (760 mg, 3 mmol) in dry trimethyl phosphate (10 mL) at 0° C. under Ar. The reaction mixture was stirred for 2 h at 0° C. then an ice-cold suspension of remdesivir riboside (1.0 g, 3.3 mmol, 1.1 equiv.) in 15 mL of trimethyl phosphate under Ar was added all at once to the rapidly stirred mixture. The resultant mixture was stirred for 6 h at 0° C., as the mixture slowly became homogeneous. The mixture was stoppered and allowed to stand in a 0° C. freezer for 12 h. The reaction mixture was placed in an ice bath under Ar and rapidly stirred while water (3.2 mL, 0.18 mol, 60 equiv.) was added. The mixture stirred in the ice bath for 2 h then triethylamine (0.8 mL, 11 mmol) was added dropwise. After stirring for 30 min. the pH was checked with the use of external damp pH paper and was found to be 1-2. Additional triethylamine was added in 0.1 mL portions and checked after each addition until the pH was 4 (c.a. 0.3 mL triethylamine added). The ice bath was removed and the mixture was allowed to stir at ambient temperature for 2-3 h; then slowly poured into 350 mL of rapidly-stirred acetonitrile to precipitate the crude product. The mixture was filtered through a sintered glass funnel and the white solids washed with 4×50 mL portions of acetonitrile to remove residual trimethyl phosphate. The white solid obtained was air-dried on the vacuum funnel for several hours. The crude product was dissolved in 8 mL of de-ionized water and the pH was adjusted to 4-5 with triethylamine.

The solution was loaded onto a 275 g Isco® reverse-phase column and purification was accomplished using reverse-phase chromatography on an Isco® automated chromatography system, eluting with a gradient of water-20% acetonitrile in water over 22 minutes which achieved baseline separation of the two desired isomers. The pure fractions containing each isomer were pooled and concentrated on the rotary evaporator to a volume of about 10 mL. The solutions were lyophilized to afford 90 mg (5%) of Compound 1 and 320 mg (17%) of Compound 2. The protonation state of the compounds may differ from how they are drawn, depending on salt form and pH of solution from which they are isolated and/or analyzed. For example, Compound 1 may exist with deprotonated phosphate and carboxylate groups, and an external cation. The structural assignment of each isomer was determined by 1H NMR analysis.

Compound 1: $^1$H NMR (D$_2$O): δ 9.10 (s, 1H), 8.87 (d, 1H), 8.71 (d, 1H), 7.93 (app t, 1H), 7.86 (s, 1H), 7.0 (dd, 2H), 5.96 (d, 1H), 4.86 (d, 1H), 4.48 (app t, 1H), 4.43 (m, 1H), 4.28 (app t, 2H), 4.23 (m, 3H), 4.06 (m, 2H), 3.87 (m, 2H). $^{31}$P NMR (D$_2$O): −0.02 ppm. MS(ESI+) m/z=608.1

Compound 2: $^1$H NMR (D$_2$O): δ 9.30 (d, 1H), 9.10 (s, 1H), 8.56 (d, 1H), 8.18 (app t, 1H), 7.89 (s, 1H), 6.72 (d, 1H), 6.42 (d, 1H), 6.14 (d, 1H), 5.23 (dd, 1H), 5.05 (d, 1H), 4.6-4.75 (m, 3H), 4.48 (d, 1H), 4.41 (m, 2H), 4.12-4.28 (m, 3H). $^{31}$P NMR (D$_2$O): −0.04 ppm. MS(ESI+) m/z=608.1

Example 1b: Synthetic Scheme

1) POCl$_3$, TMP, 0° C.
2) 2'C-methyl base
   i) base = guanosine;
   ii) base = uridine;
   iii) base = cytodine; or
   iv) base = 6-O-methyl guanoisine
3) water, triethylamine

Experimental Procedure

The experimental procedure of Example 1a was repeated with a variety of bases for coupling as shown in the synthetic scheme. Compounds 3-6 were isolated and tested according to Example 2.
Compound 3: NAR-2'C-methyl-5'-guanosine ester
Compound 4: NAR-2'C-methyl 5'-uridine ester
Compound 5: NAR-2'C-methyl-5'-cytidine ester
Compound 6: NAR-2'C-Methyl-6-O-methyl-5'-guanosine ester

Example 2: Antiviral Assay

SARS-CoV-2, USA-WA1/2020, stocks were prepared by passaging the virus in Vero 76 cells using test media of MEM supplemented with 2% FBS and 50 microgram/mL gentamicin.

Compounds to be tested were taken from powder form and solubilized in DMSO to prepare 20 mM stock solutions. Compounds were serially diluted using eight half-log dilutions in test media so that the starting (high) test concentration was 100 microMolar. Each dilution was added to 5 wells of a 96-well plate with 80-100% confluent Vero 76 cells. Three wells of each dilution were infected and untreated as virus controls, and six wells were uninfected and untreated as cell controls. SARS-CoV-2 was prepared to achieve the lowest possible multiplicity of infection (MOI) that would yield >80% cytopathic effect (CPE) within 3 days. Remdesivir was tested in parallel as a positive control. Plates were incubated at 37±2° C., 5% $CO_2$.

On day 5 post-infection, once untreated virus control wells reached CPE, plates were stained with neutral red dye for approximately 2 hours (±15 minutes). Supernatant dye was removed and wells rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated ($CC_{50}$). The selective index (SI) is the $CC_{50}$ divided by $EC_{50}$.

TABLE 1

|  | Anti-viral Assay (EC50) |
| --- | --- |
| Compound 1 | i) 17 µM |
|  | ii) 31 µM |
| Compound 2 | i) 0.71 µM |
|  | ii) 0.88 µM |
| Compound 3 | >100 µM |
| Compound 4 | >100 µM |
| Compound 5 | >100 µM |
| Compound 6 | >100 µM |
| Remdesivir (comparative compound) | 1.9-6 µM |
| GS-441524 (comparative compound) | 0.5-1.1 µM |
| Nicotinamide mononucleotide (NMN) (comparative compound) | >2000 µM |

Example 3: NAD Assay

Cellular assay: Test cells (for example, primary human fibroblasts) are seeded at 1×103 per well in 96-well tissue culture-treated dishes. Forty-eight hours later, cells are treated with either test compound, reference compound, or vehicle at a concentration of 1 mM. Cells are incubated at 37 C, 5% $CO_2$ for twenty-four hours. Viability is assessed using CellTiter-Fluor™ (Promega, Madison, Wis.). Cells are then lysed and NAD(H) content is measured using the NAD/NADH-Glo™ assay (Promega, Madison, Wis.). NAD content is normalized to the number of viable cells and expressed relative to untreated control cells.

Figure 1:
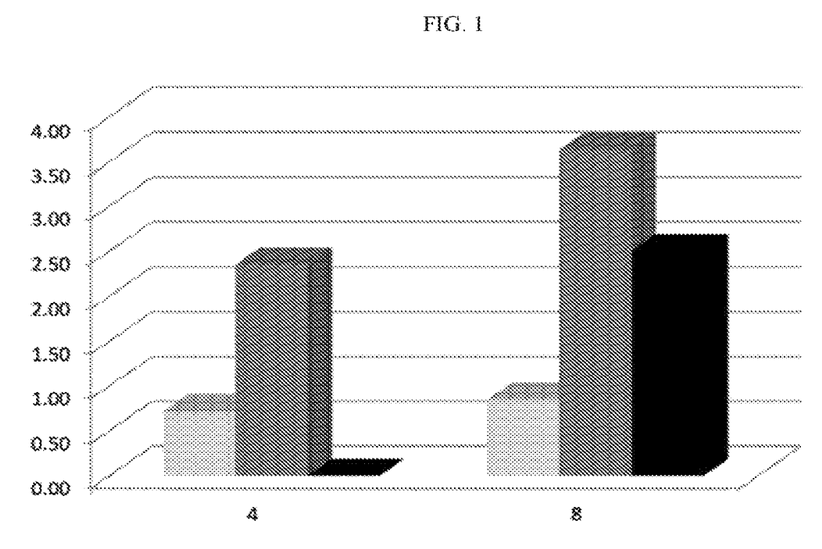
FIG. 1 provides the mean composite NAD assayed concentration in mouse liver cells. The Y-axis is concentration in mmol/kg. The X-axis shows two time points: 4 hours and 8 hours. The left-most bar at each time point is vehicle, the central bar is reference compound nicotinamide mononucleotide (NMN), and the right-most bar at each time point is Compound 2. Each compound is administered orally to mice at 500 mg/kg.
Figure 2:
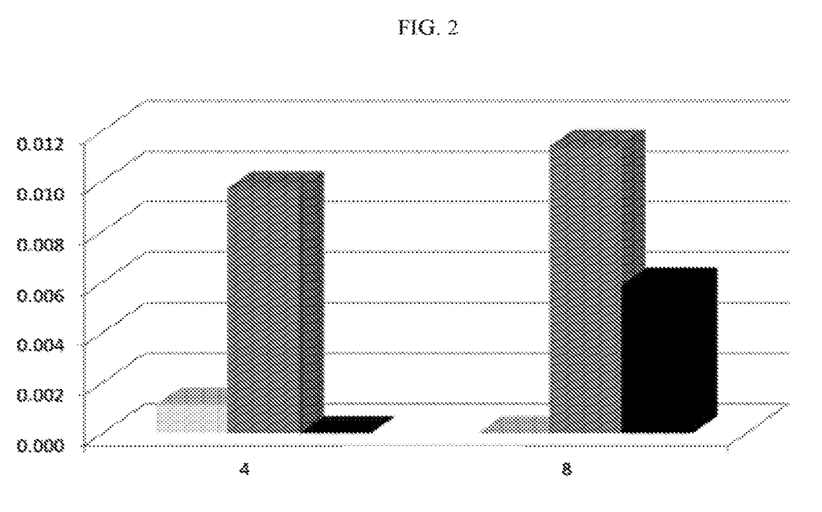
FIG. 2 provides the mean composite NAAD assayed concentration in mouse skeletal muscle cells. The Y-axis is concentration in mmol/kg. The X-axis shows two time points: 4 hours and 8 hours. The left-most bar at each time point is vehicle, the central bar is reference compound nicotinamide mononucleotide (NMN), and the right-most bar at each time point is Compound 2. Each compound is administered orally to mice at 500 mg/kg.

In vivo NAD and NAAD assay: Animals were dosed with 500 mg/kg of test compound or reference compound in vehicle. Results for Compound 2 are shown in FIGS. 1 and 2, which show that Compound 2 was orally available and boosted NAD and NAAD in murine liver and skeletal muscle, respectively, at the 8 hour time point.

INCORPORATION BY REFERENCE AND EQUIVALENTS

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:
1. A compound having the structure or a pharmaceutically acceptable salt thereof.

2. A pharmaceutically acceptable salt of the compound of claim 1, wherein the salt comprises a cation selected from $H^+$, $Li^+$, $Na^+$, $K^+$, $Mg^{2+}$, and $Ca^{2+}$.

3. A pharmaceutically acceptable salt of the compound of claim 1, wherein the salt comprises an anion selected from acetate, triflate, halide, trifluoroacetate, formate, $H_2PO_4^-$, $HPO_4^{2-}$, $OH^-$, $HSO_4^-$, $SO_4^{2-}$, $NO_3^-$, $HCO_3^-$, and $CO_3^{2-}$.

4. A pharmaceutical composition comprising a compound or pharmaceutically acceptable salt of claim 1 and one or more pharmaceutically acceptable excipients.

5. The pharmaceutical composition of claim 4, wherein the pharmaceutically acceptable excipient is selected from an anti-adherent, a binder, a coating, a dye, a disintegrant, a flavoring agent, a glidant, a lubricant, a preservative, a sorbent, a sweetener, a dispersant, a diluent, a filler, a granulating agent, a coating agent, a wax, a suspending agent, a wetting agent, a vehicle, a liquid carrier, and combinations thereof.

6. The pharmaceutical composition of claim 4, wherein the composition is in a solid form selected from a tablet, a pill, a capsule, a caplet, a troche, granules, powders, a sachet, a dry powder inhalation form, a chewable, a pastille, and a lozenge.

7. The pharmaceutical composition of claim 6, wherein the composition is in the form of a tablet.

8. The pharmaceutical composition of claim 4, wherein the compound or the pharmaceutically acceptable salt is present in the composition in an amount from about 0.001% by weight to about 90% by weight.

* * * * *